United States Patent
Miyazaki et al.

(10) Patent No.: US 9,867,846 B2
(45) Date of Patent: Jan. 16, 2018

(54) ATOPIC-DERMATITIS-SUPPRESSING FIBER, FIBER ASSEMBLY AND FIBER PRODUCT, METHOD FOR USING SAME, AND METHOD FOR SUPPRESSING ATOPIC DERMATITIS

(71) Applicants: KYOTO PREFECTURAL PUBLIC UNIVERSITY CORPORATION, Kyoto-shi, Kyoto (JP); KURASHIKI BOSEKI KABUSHIKI KAISHA, Kurashiki-shi, Okayama (JP)

(72) Inventors: Kohji Miyazaki, Kyoto (JP); Kunihiro Ohshima, Osaka (JP); Susumu Katsuen, Osaka (JP)

(73) Assignees: Kyoto Prefectural Public University Corporation, Kyoto (JP); Kurashiki Boseki Kabushiki Kaisha, Okayama (JP)

( * ) Notice: Subject to any disclaimer, the term of this patent is extended or adjusted under 35 U.S.C. 154(b) by 75 days.

(21) Appl. No.: 14/760,864

(22) PCT Filed: Jan. 21, 2014

(86) PCT No.: PCT/JP2014/051085
§ 371 (c)(1),
(2) Date: Jul. 14, 2015

(87) PCT Pub. No.: WO2014/115715
PCT Pub. Date: Jul. 31, 2014

(65) Prior Publication Data
US 2015/0352141 A1   Dec. 10, 2015

(30) Foreign Application Priority Data

Jan. 25, 2013 (JP) .................. 2013-012172

(51) Int. Cl.
*A61K 31/717* (2006.01)
*D06M 13/292* (2006.01)
*D06M 13/432* (2006.01)
*D06M 10/00* (2006.01)
*D06M 10/08* (2006.01)
*D06M 14/22* (2006.01)
*D06M 16/00* (2006.01)
*D06M 101/06* (2006.01)

(52) U.S. Cl.
CPC ......... *A61K 31/717* (2013.01); *D06M 10/008* (2013.01); *D06M 10/08* (2013.01); *D06M 13/292* (2013.01); *D06M 13/432* (2013.01); *D06M 14/22* (2013.01); *D06M 16/00* (2013.01); *D06M 2101/06* (2013.01)

(58) Field of Classification Search
None
See application file for complete search history.

(56) References Cited

U.S. PATENT DOCUMENTS

| 2008/0249044 | A1* | 10/2008 | Tanaka | A61K 9/0014 514/44 R |
|---|---|---|---|---|
| 2008/0279905 | A1 | 11/2008 | Kawamoto et al. | |
| 2009/0018105 | A1 | 1/2009 | Braxmeier et al. | |
| 2011/0263531 | A1 | 10/2011 | Braxmeier et al. | |
| 2012/0329637 | A1* | 12/2012 | Iwanade | D06M 10/008 502/5 |
| 2014/0155589 | A1 | 6/2014 | Miyazaki et al. | |

FOREIGN PATENT DOCUMENTS

| EP | 1 764 430 | 3/2007 | | |
|---|---|---|---|---|
| EP | 2 738 306 | 6/2014 | | |
| JP | 3-024178 | 2/1991 | | |
| JP | 2002-105882 | 4/2002 | | |
| JP | 2006-152464 | 6/2006 | | |
| JP | 2007-107149 | 4/2007 | | |
| JP | 2007-254910 | 10/2007 | | |
| JP | 2008-303487 | 12/2008 | | |
| JP | 2009-007691 | 1/2009 | | |
| JP | 2009-091707 | 4/2009 | | |
| JP | 2011-178844 | 9/2011 | | |
| JP | 2011178844 | A * | 9/2011 | ............... C09K 3/00 |
| JP | 2012-149360 | 8/2012 | | |
| WO | 00/27402 | 5/2000 | | |
| WO | 20061008916 | 1/2006 | | |
| WO | 2007/071402 | 6/2007 | | |

OTHER PUBLICATIONS

Simpson, E. L. (2010). Atopic dermatitis: a review of topical treatment options. Current medical research and opinion, 26(3), 633-640.*
Office Action issued in corresponding Japanese Application No. 2014-558572, dated Dec. 8, 2015, 3 pages.
International Search Report issued in International Application No. PCT/JP2014/051085, dated Apr. 8, 2014, 4 pages.
Extended European Search Report issued in corresponding European Application, dated Jun. 3, 2016, 6 pages.

* cited by examiner

Primary Examiner — Shaojia A Jiang
Assistant Examiner — Dale R Miller
(74) Attorney, Agent, or Firm — Hamre, Schumann, Mueller & Larson, P.C.

(57) ABSTRACT

The present invention relates to an atopic dermatitis suppressing fiber to which a compound containing a phosphate group is fixed by chemical bonding. The present invention further relates to an atopic dermatitis suppressing fiber assembly that includes the atopic dermatitis suppressing fiber arranged to contact skin. The present invention further relates to an atopic dermatitis suppressing fiber product that includes the atopic dermatitis suppressing fiber arranged to contact skin. The present invention further relates to a method for using the atopic dermatitis suppressing fiber and a method for suppressing atopic dermatitis that include: arranging the atopic dermatitis suppressing fiber to contact skin, thereby suppressing atopic dermatitis.

2 Claims, No Drawings

ATOPIC-DERMATITIS-SUPPRESSING FIBER, FIBER ASSEMBLY AND FIBER PRODUCT, METHOD FOR USING SAME, AND METHOD FOR SUPPRESSING ATOPIC DERMATITIS

TECHNICAL FIELD

The present invention relates to an atopic dermatitis suppressing fiber, an atopic dermatitis suppressing fiber assembly, an atopic dermatitis suppressing fiber product capable of suppressing atopic dermatitis, a method for using the atopic dermatitis suppressing fiber, and a method for suppressing atopic dermatitis.

BACKGROUND ART

Recently, in accordance with changes in living environment and eating habits, the number of people suffering from atopic dermatitis has been increasing rapidly. The pathogenetic mechanism of atopic dermatitis has not been clarified in many aspects and methods for treating atopic dermatitis have not yet been established.

Since the skin of patients with atopic dermatitis is very sensitive, undergarments, underwear and the like that directly come into contact with the skin must be less irritating to the skin. Undergarments made of general synthetic fibers tend to worsen atopic dermatitis. Also, undergarments using natural cotton sometimes worsen the symptoms of atopic dermatitis, e.g., spread of affected areas, due to wearing for a long period of time.

To cope with this, Cited Document 1 proposes a fiber structure containing amygdalin. Patent Document 2 proposes a fabric for patients with atopic dermatitis composed of specific ethylene-vinylalcohol (EVOH) fibers. Patent Document 3 proposes skin pruritus reducing underwear composed of a fiber material dyed with a turmeric extracted solution. Patent Document 4 proposes underwear for patients with atopic dermatitis having fibers made of thermoplastic elastomer, having a specific bending resistance and a specific moisture percentage, and having a specific absorption rate or a specific dispersion diameter.

PRIOR ART DOCUMENTS

Patent Documents

Patent Document 1: JP 2006-152464 A
Patent Document 2: WO 2006/008916
Patent Document 3: JP 2008-303487 A
Patent Document 4: JP 2009-7691 A

DISCLOSURE OF INVENTION

Problem to be Solved by the Invention

The present invention provides a novel atopic dermatitis suppressing fiber, atopic dermatitis suppressing fiber assembly and atopic dermatitis suppressing fiber product that are capable of suppressing atopic dermatitis, a method for using the atopic dermatitis suppressing fiber, and a method for suppressing atopic dermatitis.

Means for Solving Problem

The present invention relates to an atopic dermatitis suppressing fiber to which a compound containing a phosphate group is fixed by chemical bonding.

The present invention further relates to an atopic dermatitis suppressing fiber assembly that includes the atopic dermatitis suppressing fiber. The atopic dermatitis suppressing fiber is arranged to contact skin.

The present invention further relates to an atopic dermatitis suppressing fiber product that includes the atopic dermatitis suppressing fiber. The atopic dermatitis suppressing fiber is arranged to contact skin.

The present invention further relates to a method for using the atopic dermatitis suppressing fiber that includes: arranging the atopic dermatitis suppressing fiber to contact skin, thereby suppressing atopic dermatitis.

The present invention further relates to a method for suppressing atopic dermatitis using the atopic dermatitis suppressing fiber that includes: arranging the atopic dermatitis suppressing fiber to contact skin, thereby suppressing atopic dermatitis.

Effect of the Invention

By fixing a compound containing a phosphate group to a fiber by chemical bonding, the present invention can provide an atopic dermatitis suppressing fiber, an atopic dermatitis suppressing fiber assembly and an atopic dermatitis suppressing fiber product that are capable of suppressing atopic dermatitis. Further, according to the use method of the present invention, it is possible to suppress atopic dermatitis by using the atopic dermatitis suppressing fiber. Moreover, according to the method for suppressing atopic dermatitis of the present invention, it is possible to suppress atopic dermatitis by using the atopic dermatitis suppressing fiber.

DESCRIPTION OF THE INVENTION

In the atopic dermatitis suppressing fiber of the present invention, a compound containing a phosphate group is fixed to the fiber by chemical bonding. The atopic dermatitis suppressing fiber suppresses atopic dermatitis by contacting skin, e.g., an affected area of a patient with atopic dermatitis, thereby reducing or improving the symptoms of atopic dermatitis. Further, preferably, the atopic dermatitis suppressing fiber can suppress one or more symptoms of atopic dermatitis selected from the group consisting of (1) redness and/or bleeding; (2) crust formation and/or dryness; (3) edema; and (4) scratch and/or tissue defect.

Though there is no particular limitation, the compound containing a phosphate group is preferably at least one selected from the group consisting of phosphoric ester and a phosphoric ester salt. The ratio of the compound containing a phosphate group to the fiber is preferably in a range from 0.01 to 3 mmol/g, and more preferably in a range from 0.1 to 1.5 mmol/g. Within this range, the effect of reducing or improving the symptoms of atopic dermatitis is high and the hand of the fiber is maintained.

Though there is no particular limitation, the fiber that can be used in the present invention is preferably a cellulose fiber, a polyethylene fiber, a polypropylene fiber, a nylon fiber, a polivinyl alcohol fiber, etc., to which electron beam graft polymerization can be applied. In view of friendliness to the skin, the fiber preferably includes a cellulose fiber. Any cellulose fiber such as cotton, linen, rayon and cupra can be used, and cotton is preferred. The ratio of the cellulose fiber to the total fibers is preferably in a range from 10 to 100 mass %.

Though there is no particular limitation, the atopic dermatitis suppressing fiber can be produced as follows. Specifically, a method for producing the atopic dermatitis suppressing fiber includes: irradiating a fiber with an electron beam; and bringing a compound containing a phosphate group into contact with the fiber so that the compound is chemically bonded, preferably graft bonded, to the fiber. The electron beam irradiation step may be performed before and/or after the chemical bonding step. In either order, the compound containing a phosphate group can be chemically bonded to the fiber. After these steps, an alkali neutralization treatment may be performed as a next step. For the alkali neutralization treatment, it is preferable to use an aqueous solution of alkali metal hydroxide such as NaOH, KOH, and LiOH. It also is possible to omit the neutralization treatment by using a compound such as sodium phosphate, potassium phosphate and lithium phosphate as the compound containing a phosphate group.

When using, for example, mono(2-methacryloyloxyethyl) phosphate (also called phosphoric acid 2-(methacryloyloxy) ethyl; hereinafter referred to as "P1M") as the compound containing a phosphate group and applying P1M to a cellulose fiber, it is considered that electron beam irradiation allows P1M to be graft bonded to cellulose as shown in the formula (2) and/or (3) below, and phosphate (phosphoric ester salt) is formed by neutralization treatment as shown in the formula (4) and/or (5) below.

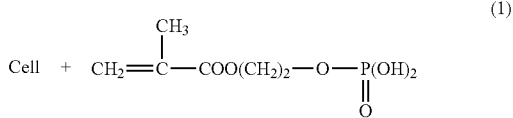

(1)

(where Cell represents cellulose; the same applies to the following)

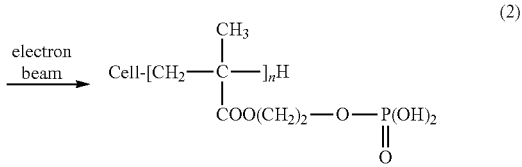

(2)

(where n is an integer of 1 or more; the same applies to the following)

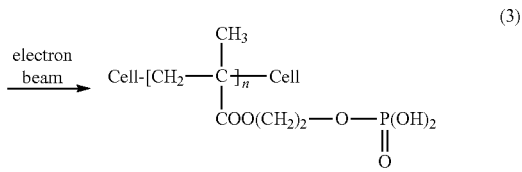

(3)

(where Cell . . . Cell represents that the compound is bonded inside a cellulose molecule; the same applies to the following)

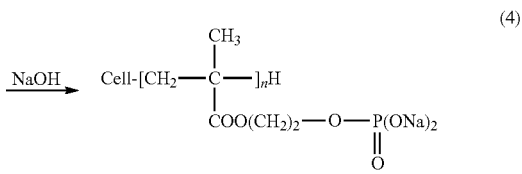

(4)

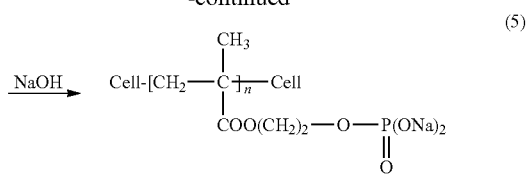

(5)

Further, in the production of the atopic dermatitis suppressing fiber, for example, by bringing an aqueous solution containing phosphoric acid and urea into contact with a cellulose fiber, the phosphoric ester may be chemically bonded, preferably covalently bonded, to the cellulose fiber. In terms of more effective introduction of phosphoric ester, by bringing an aqueous solution containing phosphoric acid and urea into contact with a cellulose fiber and heat curing the cellulose fiber, phosphoric ester is chemically bonded, preferably covalently bonded, to the cellulose fiber. For example, a cellulose fiber (fabric) is immersed in an aqueous solution containing phosphoric acid and urea (hereinafter also referred to as a phosphoric acid treatment solution, simply) so as to cause phosphoric ester to be covalently bonded to the cellulose fiber. The phosphoric acid treatment solution may contain ammonia water as needed. The pH of the phosphoric acid treatment solution can be adjusted using ammonia water. The pH of the phosphoric acid treatment solution is preferably lower than 7. The heat curing is preferably performed at a temperature from 100 to 180° C. for 0.5 to 5 minutes. For instance, by this treatment, 0.1 mass % or more, preferably 2 to 8 mass %, particularly preferably 5 to 8 mass % of phosphoric ester can be covalently bonded to the cellulose fiber. Alkali neutralization may be performed after the chemical bonding step.

A cellulose molecule is represented by the formula (6) below (where n is an integer of 1 or more). The cellulose molecule has highly reactive hydroxyl groups at C-2, C-3 and C-6 positions of glucose residue, and it is considered that phosphoric acid forms ester bonds with glucose residue at these sites. The formula (8) below shows an example where phosphoric acid forms an ester bond with glucose residue at C-2. In the formula (8), a —CH— group with which phosphoric acid forms an ester bond is a hydrocarbon group within a cellulose chain. Then, phosphate is formed by neutralization treatment as shown in the formula (9) below.

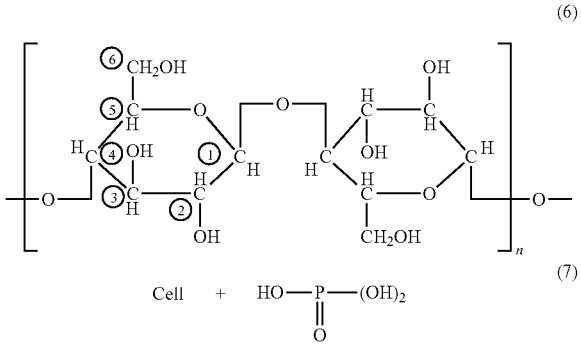

(6)

(7)

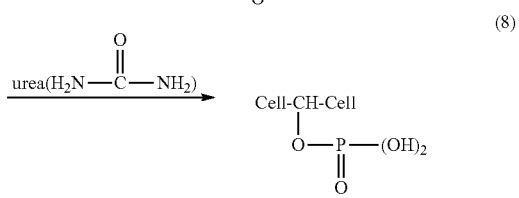

(8)

-continued

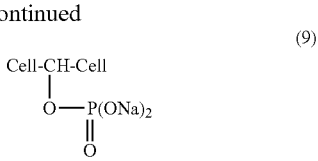
(9)

Alternatively, it is considered that phosphoric ester represented by the formulae (10) to (12) below may be formed. In the formula (10), the molar ratio between phosphorus and nitrogen is 1:1. The formulae (11) and (12) below represent phosphorus-rich ester compounds and the compound represented by the formula (12) has a crosslinked structure. It is considered that when the compounds represented by the formulae (10) to (12) are washed with diluted hydrochloric acid or diluted alkali, nitrogen is released as ammonium.

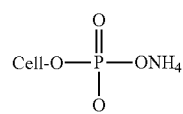
(10)

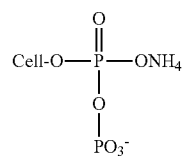
(11)

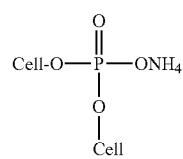
(12)

An atopic dermatitis suppressing fiber assembly of the present invention includes the atopic dermatitis suppressing fiber. The atopic dermatitis suppressing fiber is arranged so as to contact skin (arranged on a side contacting skin). In the atopic dermatitis suppressing fiber assembly, the atopic dermatitis suppressing fiber suppresses atopic dermatitis by contacting skin, e.g., an affected area of a patient with atopic dermatitis, thereby capable of reducing or improving the symptoms of atopic dermatitis, preferably capable of suppressing one or more symptoms of atopic dermatitis selected from the group consisting of (1) redness and/or bleeding; (2) crust formation and/or dryness; (3) edema; and (4) scratch and/or tissue defect. The atopic dermatitis suppressing fiber assembly may be composed only of the atopic dermatitis suppressing fiber, or may be mixed with other fibers within a range that does not impair the object of the present invention. When other fibers are mixed therein, it is preferable that the other fibers are arranged so as not to contact skin, in terms of enhancing the effect of suppressing atopic dermatitis. The shape and the structure of the fiber assembly are not limited particularly, and the fiber assembly may be in any form, including a yarn, a fabric such as a knit fabric, a woven fabric and a nonwoven fabric, a strip, a string, and the like. Specifically, it may be a gauze, a bandage, etc., and can be applied directly to an affected area of a patient with atopic dermatitis.

An atopic dermatitis suppressing fiber product of the present invention includes the atopic dermatitis suppressing fiber. The atopic dermatitis suppressing fiber is arranged so as to contact skin (arranged on a side contacting skin). In the atopic dermatitis suppressing fiber product, the atopic dermatitis suppressing fiber suppresses atopic dermatitis by contacting skin, e.g., an affected area of a patient with atopic dermatitis, thereby being capable of reducing or improving the symptoms of atopic dermatitis, preferably capable of suppressing one or more symptoms of atopic dermatitis selected from the group consisting of (1) redness and/or bleeding; (2) crust formation and/or dryness; (3) edema; and (4) scratch and/or tissue defect. The atopic dermatitis suppressing fiber product may be composed only of the atopic dermatitis suppressing fiber, or may be mixed with other fibers within a range that does not impair the object of the present invention. When other fibers are mixed therein, it is preferable that the other fibers are arranged so as not to contact skin, in terms of enhancing the effect of suppressing atopic dermatitis. As the fiber product, clothes and bedclothes are included. Examples of the clothes include underwear, undergarments, pajamas, socks, gloves and masks. Examples of the bedclothes include sheets, bed covers, pillowcases, comforters and blankets.

In the present invention, by using the atopic dermatitis suppressing fiber and, for example, bringing it into contact with skin, e.g., an affected area of a patient with atopic dermatitis, it is possible to suppress atopic dermatitis, and thus reduce or improve the symptoms of atopic dermatitis. Further, by using the atopic dermatitis suppressing fiber and, for example, bringing it into contact with skin, e.g., an affected area of a patient with atopic dermatitis, preferably, it is possible to suppress one or more symptoms of atopic dermatitis selected from the group consisting of (1) redness and/or bleeding; (2) crust formation and/or dryness; (3) edema; and (4) scratch and/or tissue defect.

EXAMPLES

Hereinafter, the present invention will be described in further detail by way of Examples. It should be noted that the present invention is not limited to the following Examples.

Example 1

<Introduction of Phosphoric Ester>

A mercerized thin fabric made from 100% cotton fiber (unit weight: 140 g/m$^2$) was immersed into an aqueous solution containing 8.5 mass % phosphoric acid (manufactured by Nacalai Tesque, Inc.) and 30 mass % urea (manufactured by Nacalai Tesque, Inc.), squeezed with a mangle until a pick up of about 70 mass % was achieved, and dried in a pin tenter at 150° C. for 90 seconds. The dried fabric was cured in the pin tenter at 165° C. for 105 seconds. The cured fabric was washed with hot water and then with water sufficiently, squeezed with the mangle, and dried in the pin tenter at 150° C. for 90 seconds. The amount of phosphate group introduced per mass of fiber, which was calculated from the difference in mass of the fabric before and after the above process and the molecular weight of phosphoric acid, was 0.54 mmol/g.

<Neutralization Treatment>

Next, the fabric to which phosphoric ester had been introduced was immersed into a 1 mass % sodium hydroxide (manufactured by Nacalai Tesque, Inc.) aqueous solution, and squeezed with the mangle until a pick up of about 70 mass % was achieved. To remove excess sodium hydroxide, the fabric was washed with hot water and then with water.

Subsequently, the fabric was squeezed with the mangle and dried in the pin tenter at 150° C. for 90 seconds.

Comparative Example 1

A mercerized thin fabric made from 100% cotton fiber (unit weight: 140 g/m²) was used as the fabric of Comparative Example 1.

The effect of suppressing atopic dermatitis achieved by the fiber of Example 1 was evaluated in an experimental system using atopic dermatitis model mice as described below. Table 1 below shows the results.

<Effect of Suppressing Atopic Dermatitis>

NCN 24 mice (female)—NC hairless mice—obtained from Oriental Yeast Co., Ltd. were used as atopic dermatitis models. 100 μL of 0.15% 1-fluoro-2,4-dinitrobenzene (DNFB) was applied to the abdomen of four NCN 24 mice (13-week old) for sensitization. After 5 days from the sensitization, 50 μL of 0.15% DNFB was applied to the back of the neck of the mice every other day to induce atopic dermatitis. After induction for 23 days, the fabric of Example 1 (length: 1 cm, width: 1.5 cm) that had been immersed in distilled water was attached to the back of the neck of the two mice, and the fabric of Comparative Example 1 (length: 1 cm, width: 1.5 cm) that had been immersed in distilled water was attached to the back of the neck of the other two mice. The fabrics were replaced with new ones every day, and the effect of suppressing atopic dermatitis was tested for three days. The symptoms of atopic dermatitis were classified into four categories: (1) redness and/or bleeding; (2) crust formation and/or dryness; (3) edema; and (4) scratch and/or tissue defect. Dermatitis scores of the respective mice were recorded and judged in accordance with the following criteria. Table 1 shows the sums of the dermatitis scores of these four categories.

(1) Redness and/or Bleeding (Observing the Symptoms of Redness and Bleeding on the Back)

0: no symptom; a state where no redness or bleeding is observed on the back

1: mild symptom: a state where redness is observed partially on the back, and bleeding in accordance with continuous scratches is not observed 2: moderate symptom: a state where redness is observed scatteringly on the back, and bleeding in accordance with continuous scratches is not observed 3: severe symptom: a state where redness is observed on the entire back, and bleeding in accordance with continuous scratches is observed (2) Crust Formation and/or Dryness (Observing the Symptoms of Crust Formation and Dryness on the Back)

0: no symptom; a state where no crust formation or dryness is observed on the back 1: mild symptom: a state where crusts are observed partially on the back, the skin is whitened slightly, and keratin is stripped off slightly 2: moderate symptom: a state where crusts are observed scatteringly on the back, and keratin is stripped off clearly 3: severe symptom: a state where crusts are observed on the entire back, and keratin is stripped off clearly (3) Edema (Observing Edema of Auricle Qualitatively)

0: no symptom; a state where neither the left nor right auricle is thickened

1: mild symptom: a state where the left or right auricle is thickened slightly

2: moderate symptom: a state where both of the auricles are thickened and swollen clearly 3: severe symptom: a state where both of the auricles are thickened, swollen and bent clearly, and they are hard when touched by fingers (4) Scratch and/or Tissue Defect (Observing the Symptoms of Scratch and Tissue Defect on Auricles)

0: no symptom; a state where no scratches or tissue defects are observed on auricles 1: mild symptom: a state where discontinuous scratches are observed on auricles, and no tissue defects are observed 2: moderate symptom: a state where continuous scratches are observed on auricles in a small area, and no tissue defects are observed 3: severe symptom: a state where continuous scratches are observed on auricles, and tissue defects are observed

TABLE 1

| | Dermatitis score | | | |
|---|---|---|---|---|
| The number of days | 0 | 1 | 2 | 3 |
| Comparative Example 1 | 11 | 12 | 10 | 6 |
| Example 1 | 10 | 10 | 7 | 3 |

As can be seen from Table 1, the fabric of Example 1 composed of the fiber to which the compound containing a phosphate group had been fixed by chemical bonding had lower dermatitis scores as compared with the fabric of Comparative Example 1 to which a phosphate group had not been introduced. It was confirmed that the fabric of Example 1 could suppress atopic dermatitis, thereby reducing or improving the symptoms of atopic dermatitis.

INDUSTRIAL APPLICABILITY

The present invention can provide gauzes, bandages, underwear, undergarments, pajamas, socks, gloves, masks, sheets, bed covers, pillowcases, comforters, blankets, and the like that are capable of reducing or improving the symptoms of atopic dermatitis.

The invention claimed is:

1. A method for suppressing atopic dermatitis, the method comprising: arranging an atopic dermatitis suppressing fabric to contact skin having atopic dermatitis, and thereby suppressing one or more symptoms of the atopic dermatitis,
   wherein the atopic dermatitis suppressing fabric is a fabric to which a compound containing a phosphate group is fixed by covalent bonding between the compound containing a phosphate group and the fabric to which the compound is fixed,
   the compound containing a phosphate group is at least one material selected from the group consisting of sodium phosphate, potassium phosphate, and lithium phosphate, and
   the one or more symptoms of the atopic dermatitis suppressed by the method are selected from the group consisting of: (1) redness, or bleeding, or a combination thereof: (2) crust formation, or dryness, or a combination thereof: (3) edema: and (4) scratch, or tissue defect, or a combination thereof.

2. The method for suppressing atopic dermatitis according to claim 1, wherein the fabric comprises a cellulose fiber.

* * * * *